United States Patent [19]

Stacpoole

[11] 4,122,188

[45] Oct. 24, 1978

[54] TREATMENT OF HYPERLIPOPROTEINEMIA WITH A DICHLOROACETATE SALT

[75] Inventor: Peter W. Stacpoole, Nashville, Tenn.

[73] Assignee: Vanderbilt University, Nashville, Tenn.

[21] Appl. No.: 828,677

[22] Filed: Aug. 29, 1977

Related U.S. Application Data

[63] Continuation-in-part of Ser. No. 754,966, Dec. 28, 1976, abandoned.

[51] Int. Cl.² ............................................. A61K 31/19
[52] U.S. Cl. .................................................... 424/317
[58] Field of Search ......................................... 424/317

[56] References Cited

U.S. PATENT DOCUMENTS 3,179,562   4/1965   Hoffman et al. ...................... 424/311

OTHER PUBLICATIONS

Chem. Abst. 84, 159,601(c) – Holloway et al., – "Phenformin . . . Dichloroacetate" (1976).
Chem. Abst. 83, 25,895(x) – Blackshear et al., "Metabolic Interaction of Dichloroacetate . . . Ketoacidosis" (1975).
Chem. Abst. 82, 68,815(t) Blackshear et al., "Metabolic Effects of Sodium Dichloroacetate . . . Rat" (1975).
Chem. Abst. 72, 77261(e) – Stacpoole et al. (1970).

*Primary Examiner*—Albert T. Meyers
*Assistant Examiner*—D. W. Robinson
*Attorney, Agent, or Firm*—Harrington A. Lackey

[57] ABSTRACT

The present invention relates to the use of salts of dichloroacetate which contain one or two molecules of dichloroacetate and one or two atoms of a mono- or divalent metallic cation, and particularly sodium dichloroacetate, for the treatment of hyperlipoproteinemia in humans.

The method of this invention has utility in the treatment of conditions in a human patient-subject in which there is abnormal elevation of the blood levels of one or more of the major lipids (cholesterol and triglycerides) normally present in the body.

6 Claims, No Drawings

TREATMENT OF HYPERLIPOPROTEINEMIA WITH A DICHLOROACETATE SALT

CROSS-REFERENCE TO RELATED APPLICATION

This application is a continuation-in-part of original application Ser. No. 754,966, filed Dec. 28, 1976, now abandoned.

BACKGROUND OF THE INVENTION

This invention relates to the treatment of hyperlipoproteinemia and more particularly to the treatment of hyperlipoproteinemia in humans with a dichloroacetate salt.

Lipoproteins consist of lipid (cholesterol or triglyceride) bound to various proteins. They are synthesized by the liver, from which they are secreted into the circulation of the blood stream. The relative proportion of lipid and protein is variable, and thus their physico-chemical properties differ. The greater the proportion of lipid, the less dense is the lipoprotein. Based on the lipid-to-protein ratio and, hence, on the density, liproproteins are classified as (from least to most dense):
1. chylomicra
2. very low density lipoproteins (VLDL)
3. low density lipoproteins (LDL)
4. intermediate low density lipoproteins (ILDL)
5. high density lipoproteins (HDL)

Based, in part, on the relative abnormal increases in the various lipoproteins, the hyperlipoproteinemias have been characterized as:
Type I (increased chylomicra)
Type IIa (increased LDL)
Type IIb (increased LDL and VLDL)
Type III (increased ILDL)
Type IV (increased VLDL)
Type V (increased chylomicra and VLDL)

The constituency of chylomicra is almost all triglycerides.

Types IIb and IV hyperlipoproteinemia are most prevalent in diabetics.

Type IIa hyperlipoproteinemia (familial hypercholesterolemia) is characterized by a high level of plasma cholesterol.

Persons with excessive amounts of cholesterol in the blood stream have a greater tendency to develop cardio-vascular diseases than persons with lower or normal levels of plasma cholesterol.

Persons with excess amounts of triglycerides in their blood stream have a greater tendency to develop pancreatitis than persons with normal levels of triglycerides.

The effects of the dichloroacetate ion on various aspects of intermediary metabolism have been studied extensively in several animal models. Among its metabolic effects, the dichloroacetate ion alters lipid metabolism in animals by inhibiting peripheral fatty acids and ketone body oxidation.

Furthermore, hyperglycemia has been reduced in animals having diabetes mellitus by treatment with alpha, alpha substituted acetic acid derivatives, including sodium dichloroacetate, as taught in U.S. Pat. No. 3,179,562, issued to Howard E. Hoffman et al on Apr. 20, 1965. The Hoffman et al patent also teaches the maintenance of glycosuria within normal limits in animals having diabetes mellitus by oral ingestion of a compound including the dichloroacetate ion.

SUMMARY OF THE INVENTION

It is therefore an object of this invention to provide a method for the treatment of hyperlipoproteinemia in human patient-subjects, with or without diabetes mellitus, by administering to the patient-subject a dichloroacetate salt, such as sodium dichloroacetate.

The sodium dichloroacetate is administered to the human patient-subject, in accordance with this invention, orally in the form of capsules or tablets in daily dosages ranging from 250 mgs. to 4000 mgs., to significantly lower the blood levels of cholesterol and triglyceride.

DESCRIPTION OF THE PREFERRED EMBODIMENTS

According to the present invention, the treatment of hyperlipoproteinemia in human patients is carried out by the use of non-toxic, non-corrosive salts of dichloroacetate, and specifically sodium dichloroacetate. The words "non-toxic" and "non-corrosive" are used in their pharmaceutical sense to mean non-injurious to the human patient.

According to this method of treatment of hyperlipoproteinemia, the route of administration is oral. The means by which the dichloroacetate salt, specifically sodium dichloroacetate in powder form, is administered is by encapsulation of the salt in gelatin, or in some other conventional inert, dissolvable material, together with an inert filler, such as lactose. The compound, such as sodium dichloroacetate in powder form, may also be formulated into a pill or tablet, also containing an inert filler, such as lactose.

The sodium dichloroacetate is administered orally in a daily dosage of a range of 250 mgs.–4000 mgs. A preferred dosage ranges from 800–4000 mgs. per day. Administration of the dosage can be spread out over several times per day, as with meals, or otherwise as convenient. The exact dosage with the recited range will depend on the severity of the hyperlipoproteinemia, upon concurrent treatments, the physiology of the human patient, other attendant circumstances, and the nature of the effect desired. The dosages may be continued until the desired reduction in blood level of the cholesterol and triglycerides has been attained.

In preparing the composition for oral administration, the dichloroacetate salt, e.g. sodium dichloroacetate, will constitute, under most circumstances, a fairly high proportion of the total composition, so that the inert filler material and carrier material will constitute a very small proportion of the total composition.

Although to date only sodium dichloroacetate has been used in the treatment of human patient-subjects with hyperlipoprotenemia, nevertheless it is believed that the treatment according to this method will be successful when the human patient-subjects are administered salts of dichloroacetate having the general formula:

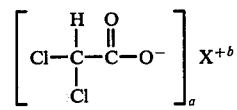

wherein:
$X$ is any mono or divalent metallic cation;
$a$ is an integer from 1 to 2, inclusive;

$b$ is an integer from 1 to 2, inclusive.

Clinical studies with hospitalized subjects with hyperlipoproteinemia have shown that treatment with the sodium salt of dichloroacetate significantly reduces the elevated blood levels of cholesterol and triglyceride. Greatest success has been achieved in patients with Type IIb or Type IV hyperlipoproteinemia. There is evidence that one mechanism by which dichloroacetate may lower blood lipoproteins is by stimulating their oxidation by the liver. Thus, no long-term deleterious effects of dichloroacetate in terms of building up liver fat stores is likely.

This invention will be further understood by reference to the following examples:

EXAMPLE 1

500 milligrams of sodium dichloroacetate is mixed with lactose filler and encapsulated into gelatin capsules in a conventional manner. From 2 to 8 such capsules are administered daily as a single oral dose to human subjects with diabetes mellitus and Type IIb or Type IV hyperlipoproteinemia. Among 10 patients so treated for a period of one week, plasma cholesterol fell an average of 19% (range +7% to −40%) from pre-treatment levels, and plasma triglyceride fell an average of 53% (range −18% to −83%) from pre-treatment levels.

EXAMPLE 2

Sodium dichloroacetate is encapsulated and administered as in Example 1 to human subjects with Type IV hyperlipoproteinemia in the absence of diabetes mellitus. In one patient so treated with a daily oral dose of 4000 milligrams of sodium dichloroacetate for a period of one week, plasma cholesterol was reduced from 215 mg/dl to 170 mg/dl, representing a change of 21%, and plasma triglyceride decreased from 237 mg/dl to 120 mg/dl, a change of 49%.

EXAMPLE 3

Sodium dichloroacetate is encapsulated and administered as in Example 1 to human subjects with Type IIa (familial hypercholesterolemia) hyperlipoproteinemia. In one patient so treated with a daily oral dose of 3,000 mg. of sodium dichloroacetate for a period of one week, plasma cholesterol fell from 578 mg/dl to 362 mg/dl, representing a 38% reduction in plasma concentration. At the same time, plasma triglyceride remained within normal limits, changing from 104 mg/dl to 70 mg/dl, a 33% decrease.

EXAMPLE 4

Sodium dichloroacetate is encapsulated and administered as in Example 1 to human subjects with Type IIb or Type IV hyperlipoproteinemia with or without co-existent diabetes mellitus. On going studies with 3 patients so treated with a daily oral dose of 1,000 or 2,000 milligrams of sodium dichloroacetate for one month indicate that normalization of plasma triglyceride and cholesterol occur by the end of dichloroacetate therapy.

Oral doses of sodium dichloroacetate have been administered in dosages as low as 800–1,000 milligrams per day for a period of six days to human patients with comparable results.

The serum insulin levels in all the above examples did not change, or else decreased, during therapy. Human patients receiving a single 1.6–4 gram dose of sodium dichloroacetate experienced transient, mild drowsiness. No other evidence of adverse effects was noted.

Examples 1 through 4, inclusive, provide evidence that sodium dichloroacetate is an effective oral agent in the treatment of various types of hyperlipoproteinemia. The rapidity of onset and magnitude of fall in plasma lipids (triglyceride and cholesterol) produced by dichloroacetate is greater than those changes achieved with other currently existing hypolipoproteinemic agents, such as clofibrate, cholestyramine, nicotinic acid and thyroxine. Dichloroacetate offers the advantage of being able to reduce both triglycerides and cholesterol in individual human patients, whereas standard lipid-lowering drugs usually reduce only one of these two lipid fractions, and to a degree less than that produced by a dichloroacetate.

Finally, dichloroacetate has the distinct potential (Example 3) of being the first oral agent shown effective in significantly reducing plasma cholesterol in Type IIa hyperlipoproteinemia (familial hypercholesterolemia), a genetic disease up to now refractory to standard drug therapy.

Because of the marked reductions in plasma lipids produced by the once daily dosing interval described in Examples 1 through 4 inclusive, it is proposed that longer dose intervals (eg., every other day) and/or reductions in a given daily dose (eg., 250 mg. or 500 mg. given once or twice daily) may be equally effective in lowering plasma triglyceride and cholesterol.

What is claimed is:

1. The method of treating hyperlipoproteinemia in human patients in need of such treatment comprising adminstering orally to the patient-subject from 240 mgs. to 4000 mgs. per day a non-toxic, non-corrosive salt having the formula:

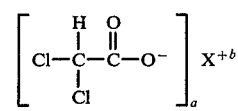

wherein:

X is any mono or divalent metallic cation;

$a$ is an integer from 1 to 2, inclusive; and $b$ is an integer from 1 to 2, inclusive.

2. The method according to claim 1 in which said compound is sodium dichloroacetate.

3. The method according to claim 2 in which said sodium dichloroacetate is administered to said patient-subject in the amount of 800–4000 mgs. per day.

4. The method according to claim 3 in which said sodium dichloroacetate is administered to said patient-subject in the amount of 1000–4000 mgs. per day.

5. The method according to claim 2 consisting of the administering of said sodium dichloroacetate to a human patient-subject having familial hypercholesterolemia.

6. The method according to claim 5 in which approximately 3000 mgs. per day of said sodium dichloroacetate is administered to said patient-subject.

* * * * *